US008989842B2

(12) United States Patent
Li et al.

(10) Patent No.: US 8,989,842 B2
(45) Date of Patent: Mar. 24, 2015

(54) SYSTEM AND METHOD TO REGISTER A TRACKING SYSTEM WITH INTRACARDIAC ECHOCARDIOGRAPHY (ICE) IMAGING SYSTEM

(75) Inventors: Dun Alex Li, Salem, NH (US); Christopher A. Nafis, Rexford, NY (US); Douglas Wildes, Ballston Lake, NY (US)

(73) Assignee: General Electric Company, Schenectady, NY (US)

( * ) Notice: Subject to any disclaimer, the term of this patent is extended or adjusted under 35 U.S.C. 154(b) by 557 days.

(21) Appl. No.: 11/860,825

(22) Filed: Sep. 25, 2007

(65) Prior Publication Data

US 2008/0287777 A1 Nov. 20, 2008

Related U.S. Application Data

(60) Provisional application No. 60/938,440, filed on May 16, 2007.

(51) Int. Cl.
*A61B 5/05* (2006.01)
*A61B 8/12* (2006.01)
(Continued)

(52) U.S. Cl.
CPC ... *A61B 8/12* (2013.01); *A61B 5/06* (2013.01); *A61B 8/483* (2013.01); *A61B 8/445* (2013.01); *Y10S 128/916* (2013.01)
USPC ............................. 600/424; 600/407; 128/916

(58) Field of Classification Search
USPC .......... 600/435, 434, 433, 407, 410, 425, 424
See application file for complete search history.

(56) References Cited

U.S. PATENT DOCUMENTS

RE30,397 E    9/1980 King
4,672,963 A   6/1987 Barken
(Continued)

FOREIGN PATENT DOCUMENTS

DE  103 40 546 A1  3/2005
EP     0602730     6/1994
(Continued)

OTHER PUBLICATIONS

Kanckstedt, C. et al, "Semi-automated 3-dimensional intracardiac echocardiography: development and initial clinical experience of a new system to guide ablation procedures", Heart Rhythm, 3 (12), pp. 1453-1459, 2006.

(Continued)

*Primary Examiner* — Nicholas Evoy

(57) ABSTRACT

A system to navigate an object traveling in an imaged subject is provided. The system includes a four-dimensional (4D) imaging system to create a first three-dimensional model of the acquired imaged data correlated relative to a time reference and defined relative to a first image coordinate system. A second imaging system creates a second three-dimensional model of the imaged subject defined relative to a second image coordinate system. A tracking system tracks movement and orientation of the object relative to a tracking coordinate system. A controller includes program instructions in combination with the processor operable to register the first and second image coordinate systems and the tracking coordinate system relative to a world coordinate system, and to combine the three-dimensional model created by the 4D imaging system with the three-dimensional model created by the second imaging system with a tracked location of the object relative to the world coordinate system.

20 Claims, 3 Drawing Sheets

(51) Int. Cl.
*A61B 5/06* (2006.01)
*A61B 8/08* (2006.01)
*A61B 8/00* (2006.01)

(56) References Cited

U.S. PATENT DOCUMENTS

| | | | |
|---|---|---|---|
| 4,722,056 A | 1/1988 | Roberts et al. | |
| 4,750,367 A | 6/1988 | Bernatets | |
| 4,834,089 A | 5/1989 | Koivukangas et al. | |
| 4,869,256 A | 9/1989 | Kanno et al. | |
| 5,099,846 A | 3/1992 | Hardy | |
| 5,203,337 A | 4/1993 | Feldman | |
| 5,241,473 A | 8/1993 | Ishihara et al. | |
| 5,353,354 A | 10/1994 | Keller et al. | |
| 5,370,120 A | 12/1994 | Oppelt et al. | |
| 5,383,454 A | 1/1995 | Bucholz | |
| 5,391,139 A | 2/1995 | Edmundson | |
| 5,391,199 A | 2/1995 | Ben-Haim | |
| 5,409,000 A | 4/1995 | Imran | |
| 5,409,007 A | 4/1995 | Saunders et al. | |
| 5,432,544 A | 7/1995 | Ziarati | |
| 5,438,997 A | 8/1995 | Sieben et al. | |
| 5,447,154 A | 9/1995 | Cinquin et al. | |
| 5,517,990 A | 5/1996 | Kalfas et al. | |
| 5,531,520 A | 7/1996 | Grimson et al. | |
| 5,558,091 A | 9/1996 | Acker et al. | |
| 5,568,384 A | 10/1996 | Robb et al. | |
| 5,568,809 A | 10/1996 | Ben-haim | |
| 5,579,764 A | 12/1996 | Goldreyer | |
| 5,588,432 A | 12/1996 | Crowley | |
| 5,608,849 A | 3/1997 | King | |
| 5,633,951 A | 5/1997 | Moshfeghi | |
| 5,662,108 A | 9/1997 | Budd et al. | |
| 5,682,890 A | 11/1997 | Kormos | |
| 5,687,737 A | 11/1997 | Branham et al. | |
| 5,713,946 A | 2/1998 | Ben-Haim | |
| 5,740,802 A | 4/1998 | Nafis et al. | |
| 5,765,561 A | 6/1998 | Chen et al. | |
| 5,771,895 A | 6/1998 | Slager | |
| 5,787,886 A | 8/1998 | Kelly | |
| 5,800,352 A | 9/1998 | Ferre et al. | |
| 5,810,008 A | 9/1998 | Dekel et al. | |
| 5,823,958 A | 10/1998 | Truppe | |
| 5,840,031 A | 11/1998 | Crowley | |
| 5,891,034 A | 4/1999 | Bucholz | |
| 5,924,989 A | 7/1999 | Polz | |
| 5,957,941 A * | 9/1999 | Ream | 606/159 |
| 5,961,454 A | 10/1999 | Kooy et al. | |
| 5,967,980 A | 10/1999 | Ferre et al. | |
| 5,978,696 A | 11/1999 | VomLehn et al. | |
| 5,999,840 A | 12/1999 | Grimson et al. | |
| 6,006,126 A | 12/1999 | Cosman | |
| 6,016,439 A | 1/2000 | Acker | |
| 6,019,725 A | 2/2000 | Vesely et al. | |
| 6,066,096 A * | 5/2000 | Smith et al. | 600/439 |
| 6,073,043 A | 6/2000 | Schneider | |
| 6,086,532 A | 7/2000 | Panescu et al. | |
| 6,102,863 A | 8/2000 | Pflugrath et al. | |
| 6,149,592 A | 11/2000 | Yanof et al. | |
| 6,168,565 B1 | 1/2001 | Napolitano | |
| 6,200,269 B1 | 3/2001 | Lin et al. | |
| 6,203,497 B1 | 3/2001 | Dekel et al. | |
| 6,216,027 B1 | 4/2001 | Willis et al. | |
| 6,226,543 B1 | 5/2001 | Gilboa et al. | |
| 6,235,038 B1 | 5/2001 | Hunter et al. | |
| 6,241,667 B1 * | 6/2001 | Vetter et al. | 600/407 |
| 6,246,898 B1 | 6/2001 | Vesely et al. | |
| 6,259,942 B1 | 7/2001 | Westermann et al. | |
| 6,259,943 B1 | 7/2001 | Cosman et al. | |
| 6,325,759 B1 | 12/2001 | Pelissier | |
| 6,351,573 B1 | 2/2002 | Schneider et al. | |
| 6,379,302 B1 | 4/2002 | Kessman et al. | |
| 6,389,311 B1 | 5/2002 | Whayne et al. | |
| 6,413,219 B1 | 7/2002 | Avila et al. | |
| 6,443,894 B1 * | 9/2002 | Sumanaweera et al. | 600/443 |
| 6,447,450 B1 | 9/2002 | Olstad | |
| 6,505,063 B2 | 1/2003 | Van Den Brink et al. | |
| 6,530,888 B2 * | 3/2003 | Smith et al. | 600/463 |
| 6,537,217 B1 | 3/2003 | Bjaerum et al. | |
| 6,572,551 B1 * | 6/2003 | Smith et al. | 600/459 |
| 6,575,901 B2 | 6/2003 | Stoycos et al. | |
| 6,592,520 B1 * | 7/2003 | Peszynski et al. | 600/437 |
| 6,650,927 B1 | 11/2003 | Keidar | |
| 6,669,635 B2 | 12/2003 | Kessman et al. | |
| 6,679,847 B1 | 1/2004 | Robinson et al. | |
| 6,705,992 B2 | 3/2004 | Gatzke | |
| 6,711,429 B1 * | 3/2004 | Gilboa et al. | 600/407 |
| 6,716,166 B2 * | 4/2004 | Govari | 600/437 |
| 6,728,562 B1 | 4/2004 | Budd et al. | |
| 6,735,465 B2 * | 5/2004 | Panescu | 600/509 |
| 6,746,401 B2 * | 6/2004 | Panescu | 600/439 |
| 6,773,402 B2 | 8/2004 | Govari et al. | |
| 6,773,408 B1 | 8/2004 | Acker et al. | |
| 6,775,404 B1 | 8/2004 | Pagoulatos et al. | |
| 6,788,967 B2 * | 9/2004 | Ben-Haim et al. | 600/424 |
| 6,902,528 B1 | 6/2005 | Garibaldi et al. | |
| 6,950,689 B1 | 9/2005 | Willis et al. | |
| 6,970,733 B2 * | 11/2005 | Willis et al. | 600/424 |
| 7,072,707 B2 * | 7/2006 | Galloway et al. | 600/424 |
| 7,090,639 B2 | 8/2006 | Govari | |
| 7,156,816 B2 | 1/2007 | Schwartz et al. | |
| 7,225,012 B1 * | 5/2007 | Susil et al. | 600/414 |
| 7,263,397 B2 | 8/2007 | Hauck et al. | |
| 7,270,634 B2 | 9/2007 | Scampini et al. | |
| 7,285,117 B2 | 10/2007 | Krueger et al. | |
| 7,306,593 B2 * | 12/2007 | Keidar et al. | 606/34 |
| 7,314,446 B2 | 1/2008 | Byrd et al. | |
| 7,485,115 B2 | 2/2009 | Nakamura | |
| RE41,066 E | 12/2009 | Martinelli et al. | |
| 7,652,259 B2 * | 1/2010 | Kimchy et al. | 250/370.08 |
| 7,657,300 B2 | 2/2010 | Hunter et al. | |
| 7,697,972 B2 * | 4/2010 | Verard et al. | 600/424 |
| 7,760,926 B2 * | 7/2010 | Boese et al. | 382/131 |
| 7,844,320 B2 | 11/2010 | Shahidi | |
| 7,995,819 B2 * | 8/2011 | Vaillant et al. | 382/128 |
| 8,050,739 B2 * | 11/2011 | Eck et al. | 600/424 |
| 8,126,239 B2 * | 2/2012 | Sun et al. | 382/131 |
| 8,175,680 B2 * | 5/2012 | Panescu | 600/424 |
| 8,412,307 B2 * | 4/2013 | Willis et al. | 600/424 |
| 8,428,690 B2 * | 4/2013 | Li et al. | 600/424 |
| 8,568,406 B2 * | 10/2013 | Harlev et al. | 606/41 |
| 8,611,983 B2 * | 12/2013 | Glossop | 600/424 |
| 2001/0029334 A1 | 10/2001 | Graumann et al. | |
| 2002/0005719 A1 | 1/2002 | Gilboa et al. | |
| 2002/0013529 A1 * | 1/2002 | Smith et al. | 600/443 |
| 2002/0026118 A1 | 2/2002 | Govari | |
| 2002/0042571 A1 | 4/2002 | Gilboa et al. | |
| 2002/0049375 A1 * | 4/2002 | Strommer et al. | 600/407 |
| 2003/0013958 A1 | 1/2003 | Govari et al. | |
| 2003/0045795 A1 | 3/2003 | Bjaerum et al. | |
| 2003/0074011 A1 | 4/2003 | Gilboa et al. | |
| 2003/0093067 A1 * | 5/2003 | Panescu | 606/32 |
| 2003/0120318 A1 | 6/2003 | Hauck | |
| 2003/0158477 A1 * | 8/2003 | Panescu | 600/424 |
| 2003/0163045 A1 | 8/2003 | Gatzke | |
| 2003/0176778 A1 | 9/2003 | Messing et al. | |
| 2003/0208102 A1 | 11/2003 | Gilboa | |
| 2003/0208123 A1 * | 11/2003 | Panescu | 600/431 |
| 2003/0231789 A1 * | 12/2003 | Willis et al. | 382/128 |
| 2004/0097805 A1 | 5/2004 | Verard | |
| 2004/0097806 A1 | 5/2004 | Hunter et al. | |
| 2004/0102769 A1 | 5/2004 | Schwartz et al. | |
| 2004/0127798 A1 | 7/2004 | Dala-Krishna et al. | |
| 2004/0138548 A1 | 7/2004 | Strommer et al. | |
| 2004/0147842 A1 | 7/2004 | Desmarais | |
| 2004/0152974 A1 | 8/2004 | Solomon | |
| 2004/0162507 A1 | 8/2004 | Govari | |
| 2004/0162550 A1 | 8/2004 | Govari et al. | |
| 2004/0186369 A1 * | 9/2004 | Lam | 600/407 |
| 2004/0204650 A1 * | 10/2004 | Taylor | 600/459 |
| 2004/0249259 A1 | 12/2004 | Heimdal et al. | |
| 2004/0254458 A1 | 12/2004 | Govari | |
| 2005/0080336 A1 * | 4/2005 | Byrd et al. | 600/428 |
| 2005/0090745 A1 | 4/2005 | Steen | |

(56) References Cited

U.S. PATENT DOCUMENTS

| | | | |
|---|---|---|---|
| 2005/0096543 A1 | 5/2005 | Jackson et al. | |
| 2005/0107688 A1* | 5/2005 | Strommer | 600/424 |
| 2005/0131474 A1 | 6/2005 | Byrd et al. | |
| 2005/0165279 A1 | 7/2005 | Adler et al. | |
| 2005/0171428 A1 | 8/2005 | Fichtinger et al. | |
| 2005/0197557 A1 | 9/2005 | Strommer et al. | |
| 2005/0203375 A1 | 9/2005 | Willis et al. | |
| 2006/0041180 A1 | 2/2006 | Viswanathan et al. | |
| 2006/0058647 A1* | 3/2006 | Strommer et al. | 600/434 |
| 2006/0182320 A1 | 8/2006 | Peszynski et al. | |
| 2006/0184016 A1 | 8/2006 | Glossop | |
| 2006/0229594 A1 | 10/2006 | Francischelli et al. | |
| 2006/0241445 A1* | 10/2006 | Altmann et al. | 600/443 |
| 2006/0253024 A1 | 11/2006 | Altmann et al. | |
| 2006/0253029 A1 | 11/2006 | Altmann et al. | |
| 2006/0253030 A1 | 11/2006 | Altmann et al. | |
| 2006/0253031 A1 | 11/2006 | Altmann et al. | |
| 2006/0253032 A1 | 11/2006 | Altmann et al. | |
| 2006/0287890 A1 | 12/2006 | Stead et al. | |
| 2007/0027390 A1* | 2/2007 | Maschke et al. | 600/425 |
| 2007/0043338 A1* | 2/2007 | Moll et al. | 606/1 |
| 2007/0130287 A1 | 6/2007 | Kumar et al. | |
| 2007/0167821 A1 | 7/2007 | Lee et al. | |
| 2007/0287902 A1 | 12/2007 | Fuimaono et al. | |
| 2008/0177994 A1 | 7/2008 | Mayer | |

FOREIGN PATENT DOCUMENTS

| | | |
|---|---|---|
| EP | 1 637 070 A | 3/2005 |
| WO | 9107726 | 5/1991 |
| WO | WO 92/19157 | 11/1992 |
| WO | 9625881 | 8/1996 |
| WO | 9729682 | 8/1997 |
| WO | 9900052 | 1/1998 |
| WO | 9824065 | 6/1998 |
| WO | 9835720 | 8/1998 |
| WO | 9958055 | 11/1999 |
| WO | 0023000 | 4/2000 |
| WO | 0056215 | 9/2000 |
| WO | WO 01/20552 A1 | 3/2001 |
| WO | 0134050 | 5/2001 |

OTHER PUBLICATIONS

Proulx, T. L. et al, "Advances in Catheter-Based Ultrasound Imaging", IEEE International Ultrasonics Symposium Proceedings, 2005.
Rotger, D. et al, "Multimodal Registration of Intravascular ultrasound Images and Angiography", Computer Vision Center Universitat Autonoma de Barcelona Bellaterra, Spain, www.cvc.uab.es/~petia/caseib2002.pdf.
Huang, X. et al, "Dynamic 3D Ultrasound and MR Image Registration of the Beating Heart", MICAI, LNCS 3750, pp. 171-178, 2005.
Martin, R. et al, "A Miniature Position and Orientation Locator for Three Dimensional Echocardiography", IEEE Proceedings on Computer in Cardiology, pp. 25-28, 1993.
Beaseley, R. A. et al, "Registration of ultrasound images", www.tgt.vanderbilt.edu/archive/Registration of ultrasound images.pdf.
Leotta, D. F. et al, "Three-Dimensional Ultrasound Imaging Using Multiple Magnetic Tracking Systems and Miniature Magnetic Sensors", IEEE on Ultrasonics Symposium, pp. 1415-1418, 1995.
Pagoulatos, N. et al, "Interactive 3-D Registration of Ultrasound and Magnetic Resonance Images Based on a Magnetic Position Sensor", Iee on Info. Tech. in Biomedicine, vol. 3, No. 4, 1999.
Beasley R. A. et al; "Registration of ultrasound images"; 8 pgs.
Bricault Ivan et al; "Registration of Real and CT-Derived Virtual Bronchoscopic Images to Assist Transbronchial Biopsy"; IEEE Transactions on Medical Imaging, Vol. 17, No. 5, Oct. 1998; 12 pgs.
"Catheter Ablation"; Heart and Vascular Institute; www.clevelandclinic.org/heartcenter; 5 pgs.

Grimson W.E.L. et al; "An Automatic Registration Method for Frameless Stereotaxy, Image Guided Surgery, and Enhanced Reality Visualization": IEEE Transactions on Medical Imaging, vol. 15, No. 2, Apr. 1996; 12 pgs.
Reinhardt, H. et al; "Computer aided surgery with special focus on neuronavigation" Computerized Medical Imaging and Graphics 23(1999) 237-244; www.elsevier.com; 8 pgs.
Huang, Xishi et al; "Dynamic 3D Ultrasound and MR Image Registration of the Beating Heart"; 8 pgs.
Birkfellner, Wolfgang et al; "Calibration of Tracking Systems in a Surgical Environment"; IEEE Transactions on Medical Imaging, vol. 17, No. 5, Oct. 1998; 6 pgs.
Yamashita Juli et al; "A 3-D Navigation System for Endoscopic Sinus Surgery"; 8 pgs.
Office Action dated Feb. 5, 2008; U.S. Appl. No. 11/182,910; filed Jul. 15, 2008; Applicant: Donaldson et al.; 10 pages.
Office Action dated Feb. 28, 2008; U.S. Appl. No. 11/433,951; filed May 15, 2006; Applicant: Donaldson; 11 pages.
Office Action dated Jan. 16, 2008; U.S. Appl. No. 11/182,473; filed Jul. 15, 2008; Applicant: Donaldson; 11 pages.
A. Milkowski et al. "Speckle Reduction Imaging"; Technical White Paper—General Electric Health Care (Ultrasound). Last accessed on Jul. 9, 2009. Available at http:www.gehealthcare.com/usen/ultrasound/education/docs/whitepaper_SRI.pdf.
http://medical.merrian-webster.com/medical/m-mode.
Radiology, vol. 121, 157-162, Copyright © 1976 by Radiological Society of North America.
Yamashita Juli et al; "Real-Time 3-D Model-Based Navigation System for Endoscopic Paranasal Sinus Surgery"; IEEE Transactions on Biomedical Engineering vol. 46, No. 1, Jan. 1999; 11 pgs.
Knackstedt, Christian MD et al; "Semi-automated 3-dimensional intracardiac echocardiography: Development and initial clinical experience of a new system to guide ablation procedures" 1547-5271/$—see front matter © 2006 Heart Rhythm Society; 7 pgs.
Leotta, Daniel F. et al; "Three-Dimensional Ultrasound Imaging Using Multiple Magnetic Tracking Systems and Miniature Magnetic Sensors"; IEEE Ultrasonics Symposium 1995; 4 pgs.
Lewis, Judith Thomas et al; "An Ultrasonic Approach to Localization of Fiducial Markers for Interactive, Image-Guided Neurosurgery—Part I: Principles" IEEE Transactions on Biomedical Engineering, vol. 45, No. 5, May 1998; 11 pgs.
Pagoulatos, Niko et al; "Interactive 3-D Registration of Ultrasound and Magnetic Resonance Images Based on a Magnetic Position Sensor"; IEEE Transactions on Technology in Biomedicine, vol. 3, No. 4, Dec. 1999; 11 pgs.
Roberts, David W.; "The Future of Frameless Stereotaxy"; Chapter 214, Textbook of Steriotactic and Functional Neurosurgery; McGraw-Hill 1998; 11 pgs.
St-Jean, Philippe et al; "Automated Atlas Integration and Interactive Three-Dimenstional Visualization Tools for Planning and Guidance in Functional Neurosurgery"; IEEE Transactions on Medical Imaging, vol. 17, No. 5, Oct. 1998; 9 pgs.
Proulx, T. L. et al; "Advances in Catheter-Based Ultrasound Imaging Intracardiac Echocardiography and the ACUSON AcuNav(TM) Ultrasound Catheter"; IEEE International Ultrasonics Symposium 1995; 10 pgs.
Sato, Yoshinobu Sato et al; "Image Guidance of Breast Cancer Surgery Using 3-D Ultrasound Images and Augmented Reality Visualization"; IEEE Transactions on Medical Imaging, vol. 17, No. 5, Oct. 1998, 13 pgs.
Schreiner, Steven et al; "An Ultrasonic Approach to Localization of Fiducial Markers for Interactive, Image-Guided Neurosurgery—Part II: Implementation and Automation"; IEEE Transaction on Biomedical Engineering, vol. 45, No. 5, May 1998; 11 pgs.
Stoll, Jeffrey et al; "Passive Markers for Ultrasound Tracking of Surgical Instruments"; J. Duncan and G. Gerig (Eds.): Miccai 2005, LNCS 3750, pp. 41-48, 2005. © Springer-Verlag Berlin Heidelberg 2005; 8 pgs.

* cited by examiner

SYSTEM AND METHOD TO REGISTER A TRACKING SYSTEM WITH INTRACARDIAC ECHOCARDIOGRAPHY (ICE) IMAGING SYSTEM

RELATED APPLICATIONS

This application claims priority to Provisional Application No. 60/938,440 filed on May 16, 2007, and hereby incorporates herein by reference in its entirety.

BACKGROUND OF THE SUBJECT MATTER

The subject matter herein generally relates to medical imaging, and more specifically, to a system and method to register models acquired by different imaging systems relative to a common reference system and synchronized with respect to time of acquisition to a common time reference.

Image-guided surgery is a developing technology that generally provides a surgeon with a virtual roadmap into a patient's anatomy. This virtual roadmap allows the surgeon to reduce the size of entry or incision into the patient, which can minimize pain and trauma to the patient and result in shorter hospital stays. Examples of image-guided procedures include laparoscopic surgery, thoracoscopic surgery, endoscopic surgery, etc. Types of medical imaging systems, for example, computerized tomography (CT), magnetic resonance (MR), positron emission tomography (PET), ultrasound (US), radiological machines, etc., can be useful in providing static or interventional image guiding assistance to medical procedures. The above-described imaging systems can provide two-dimensional or three-dimensional images that can be displayed to provide a surgeon or clinician with an illustrative map of an area of interest of a patient's body.

A drawback of the above-described imaging systems is that acquired image data can be subject to variable interpretation relative to one another.

BRIEF DESCRIPTION OF THE SUBJECT MATTER

There is a need for a system to track and navigate the position and movement of a surgical instrument or tool (e.g., a catheter) simultaneously relative to real-time generated images or models of the patient's anatomy. Generally, as a surgeon moves the medical instrument with respect to the patient's anatomy, virtual images of the instrument or object are displayed simultaneously relative to real-time acquired image data represented in the model of the patient's anatomy. The system and method of tracking should be able to readily track the spatial relationship of the medical instruments or objects traveling through an operating space of patient. The system and method should also be able to provide tracking of the tool relative to real-time images enhanced with fusion or combination or overlaying with image data acquired by other imaging systems that may compensate for deficiencies in the image data acquired by the real-time imaging system.

The above-mentioned need is addressed by the embodiments of the subject matter described herein in the following description.

According to one embodiment, a system to navigate an image-guided object traveling in an area of interest of an imaged subject in relation to an acquired image of the imaged subject is provided. The system comprises an intracardiac echocardiography (ICE) imaging system operable to create a four-dimensional model representative of a first three-dimensional model of the acquired imaged data correlated relative to a time reference and defined in spatial relation and orientation relative to a first image coordinate system. The system also includes a second imaging system different than the ICE imaging system, the second imaging system operable to create a second three-dimensional model of the imaged subject, the second three-dimensional model defined in spatial relation and orientation relative to a second image coordinate system. A tracking system is operable to track movement and orientation of the object through the imaged subject relative to a tracking coordinate system. A controller is electrically connected in communication with the ICE imaging system, the second imaging system, and the tracking system. The controller includes a processor operable to execute a plurality of program instructions stored in a memory, the plurality of program instructions in combination with the processor operable to: register the first and second image coordinate systems and the tracking coordinate system relative to a world coordinate system, and combine the four-dimensional model created by the ICE imaging system with the second three-dimensional model created by the second imaging system with a virtual image representative of a tracked location of the object relative to the world coordinate system.

According to another embodiment, a method of navigating a tool through an area of interest of an imaged subject is provided. An embodiment of the method comprises the acts of generating a four-dimensional model of the region of interest of the imaged subject with an intracardiac echocardiography (ICE) imaging system with image data acquired via the tool, the four-dimensional model correlated to a time reference and a first coordinate system; generating a three-dimensional model of the imaged subject with a second imaging system different than the ICE imaging system, the three-dimensional model of the imaged subject correlated to a second image coordinate system; tracking movement and orientation of the tool traveling through the imaged subject relative to a tracking coordinate system; registering the first and second image coordinate systems and the tracking coordinate system relative to a world coordinate system; and combining the four-dimensional model created by the ICE imaging system with the second three-dimensional model created by the second imaging system with a virtual image representative of a tracked location of the tool relative to a world coordinate system.

Systems and methods of varying scope are described herein. In addition to the aspects and advantages described in this summary, further aspects will become apparent by reference to the drawings and with reference to the detailed description that follows.

DETAILED DESCRIPTION OF THE SUBJECT MATTER

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
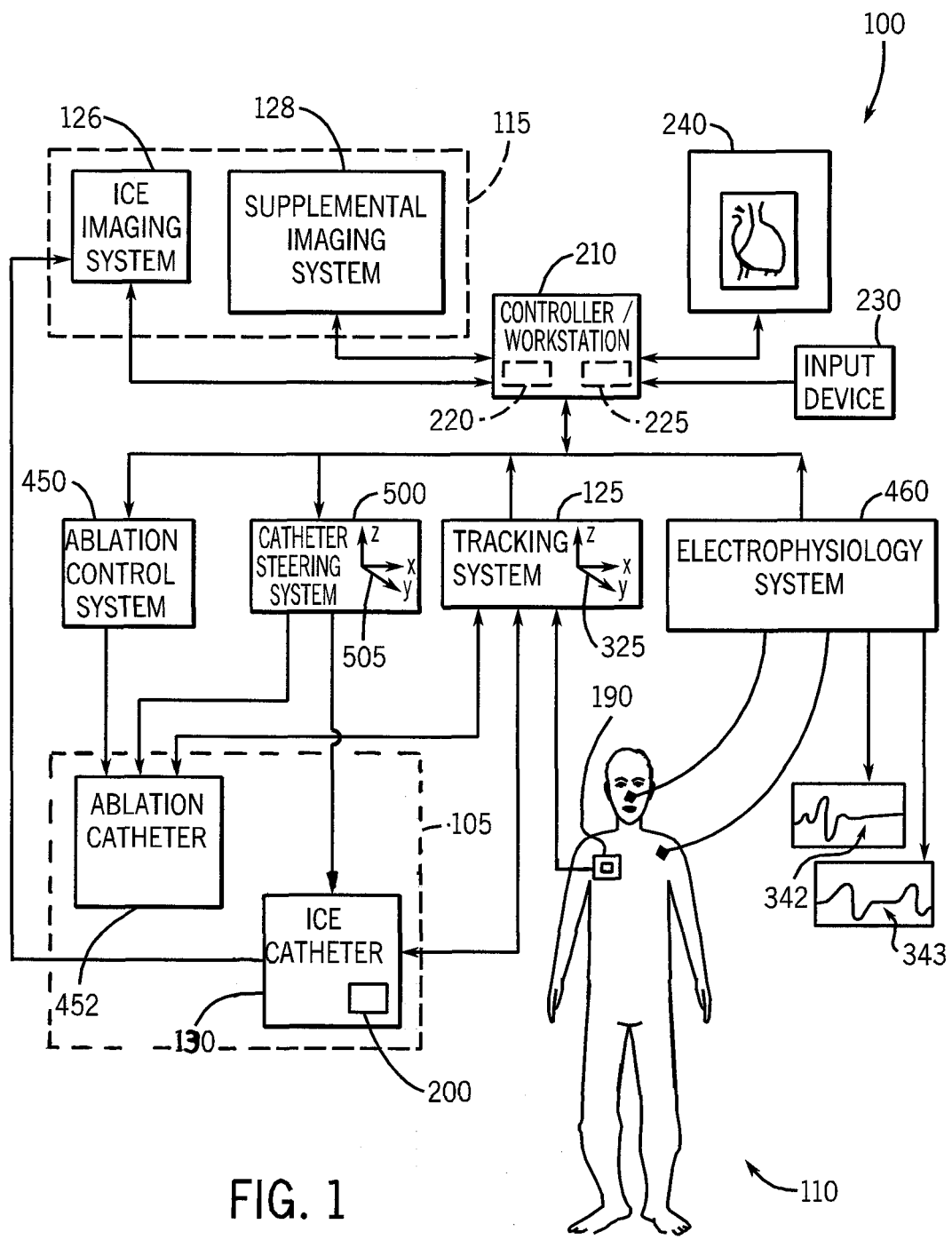
FIG. 1 illustrates a schematic diagram of an embodiment of a system described herein to perform imaged guided procedures on an imaged subject.

FIG. 1 illustrates an embodiment of a system 100 operable to track movement of a tool or object 105 through an anatomy of an imaged subject 110. The system 100 generally includes an image acquiring system or device 115, and a tracking system 125 operable to track or monitor a position of the object or tool 105 traveling through the imaged subject 110.

The image acquiring system 115 is generally operable to generate a two-dimensional, three-dimensional, or four-dimensional image data corresponding to an area of interest of the imaged subject 110. Examples of the image acquiring system 115 can include, but is not limited to, computed tomography (CT), magnetic resonance imaging (MRI), x-ray or radiation, positron emission tomography (PET), computerized tomosynthesis (CT), ultrasound (US), angiographic, fluoroscopic, and the like or combination thereof. The image acquiring system 115 can be operable to generate static images acquired by static imaging detectors (e.g., CT systems, MRI systems, etc.) prior to a medical procedure, or real-time images acquired with real-time imaging detectors (e.g., angioplastic systems, laparoscopic systems, endoscopic systems, etc.) during the medical procedure. Thus, the types of images can be diagnostic or interventional.

An exemplary image acquiring system 115 includes a real-time, intracardiac echocardiography (ICE) imaging system 126 that employs ultrasound to acquire image data of the patient's anatomy and to merge acquired image data to generate a three-dimensional model of the patient's anatomy relative to time, generating herein referred to as a four-dimensional (4D) volume or model or image. In accordance with another embodiment, the image acquiring system 115 is operable to combine (e.g., superimpose, overlay, fuse, etc.) acquired imaged data using above-described ICE imaging system 126 with pre-acquired image data or image models (e.g., two- or three-dimensional reconstructed image models) generated by another type of supplemental imaging system 128, examples of which are described above (e.g., CT, MR, PET, etc.). Although the following description refers specifically to 4D ICE imaging, the imaging system 126 can also be directed to 4D ultrasound imaging and guidance of objects 105 in other parts of the body (e.g. liver or aorta), 4D transesophageal (TEE) imaging, 4D trans-rectal imaging directed to prostate diagnostics and procedures, 4D trans-vaginal imaging, 4D laparoscopic imaging, and other types of 4D ultrasound imaging applications using a transducer held external of the imaged subject 110.

The tool or object 105 can be a surgical tool, navigational tool, a guidewire, a catheter, an endoscopic tool, a laparoscopic tool, ultrasound probe, pointer, aspirator, coil, or the like employed in a medical procedure (e.g., ablation of tissue). Yet, the type of tool 105 can vary.

Figure 2:
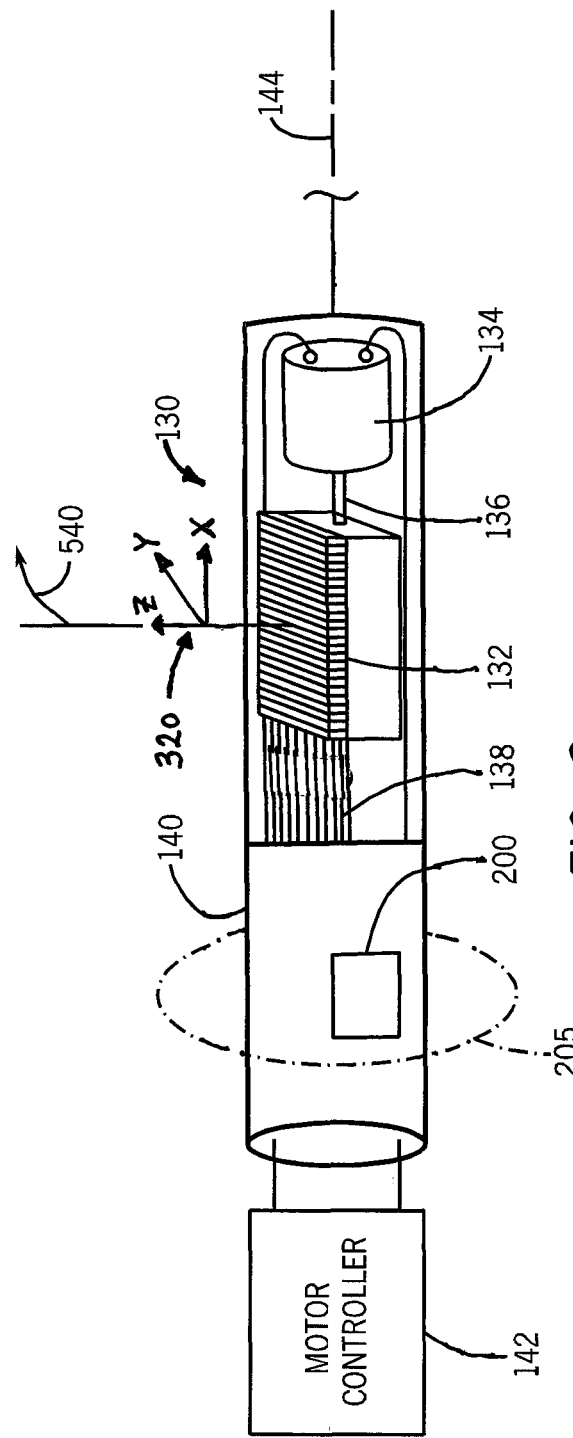
FIG. 2 illustrates a picture of a tool to travel through the imaged subject.

Referring to FIG. 2, an embodiment of the tool 105 includes an ICE catheter 130 operable to acquire 3D or 4D intracardiac echocardiography (ICE) image data of the imaged subject 110 (See FIG. 1). The illustrated embodiment of the ICE catheter 130 includes a transducer array 132, a micromotor 134, a drive shaft or other mechanical connection 136 between the micromotor 134 and the transducer array 132, an interconnect 138, and a catheter housing 140.

According to the depicted embodiment, the micromotor 134 via the drive shaft 136 generally rotates the transducer array 132. The rotational motion of the transducer array 132, is controlled by a motor controller 142 of the micromotor 134. The interconnect 138 generally refers to, for example, cables and other connections coupling so as to receive and/or transmit signals between the transducer array 132 and the ICE imaging system (shown in FIG. 1) 126. An embodiment of the interconnect 138 is configured to reduce its respective torque load on the transducer array 132 and the micromotor 134.

Still referring to FIG. 2, an embodiment of the catheter housing 140 generally encloses the transducer array 132, the micromotor 134, the drive shaft 136, and the interconnect 138. The catheter housing is generally of a material, size, and shape adaptable to internal imaging applications and insertion into regions of interest of the imaged subject 110. At least a portion of the catheter housing 140 that intersects the ultrasound imaging volume or scanning direction is comprised of acoustically transparent (e.g., low attenuation and scattering, acoustic impedance near that of the blood and tissue (Z~1.5M Rayl) material. An embodiment of the space between the transducer array 132 and the housing 140 is filled with acoustic coupling fluid (e.g., water) having an acoustic impedance and sound velocity near those of blood and tissue (e.g., Z~1.5M Rayl, V~1540 m/sec).

An embodiment of the transducer array 132 is a 64-element one-dimensional array having 0.110 mm azimuth pitch, 2.5 mm elevation, and 6.5 MHz center frequency. An embodiment of the transducer array 132 is electronically phased in order to acquire image data along a sector or plane generally parallel to the longitudinal axis 144 of the catheter housing 140. In operation, the micromotor 134 mechanically rotates the transducer array 132 about the longitudinal axis 144. The rotating transducer array 132 captures a plurality of two-dimensional images for transmission to the ICE imaging system 126 (shown in FIG. 1). The ICE imaging system 126 is generally operable to assemble the sequence or succession of acquired two-dimensional images so as to generally produce or generate a three-dimensional image or reconstructed image model of the imaged subject 110.

The rate of rotation of the transducer array 132 about the longitudinal axis 144 (generally coincidental with rotational axis) of the ICE catheter 130 is generally regulated by the motor controller 142 via the micromotor 132. For example, the motor controller 142 instructs the micromotor 134 to rotate the transducer array 132 relatively slowly to produce a three-dimensional reconstructed image model. In contrast, the motor controller 142 instructs the micromotor 134 to rotate the transducer array 132 relatively faster to produce a real-time three-dimensional reconstructed image, referred to as a four-dimensional image correlated to a general instantaneous time. The motor controller 142 is also generally operable to vary the direction of rotation so as to generally create an oscillatory motion of the transducer array 132. In this manner, the range of motion and imaged volume are restricted such that the transducer array 132 can focus on imaging a specific region and can update the 3D image of that region more frequently, thereby providing a real-time 3D, or 4D, image.

Figure 3:
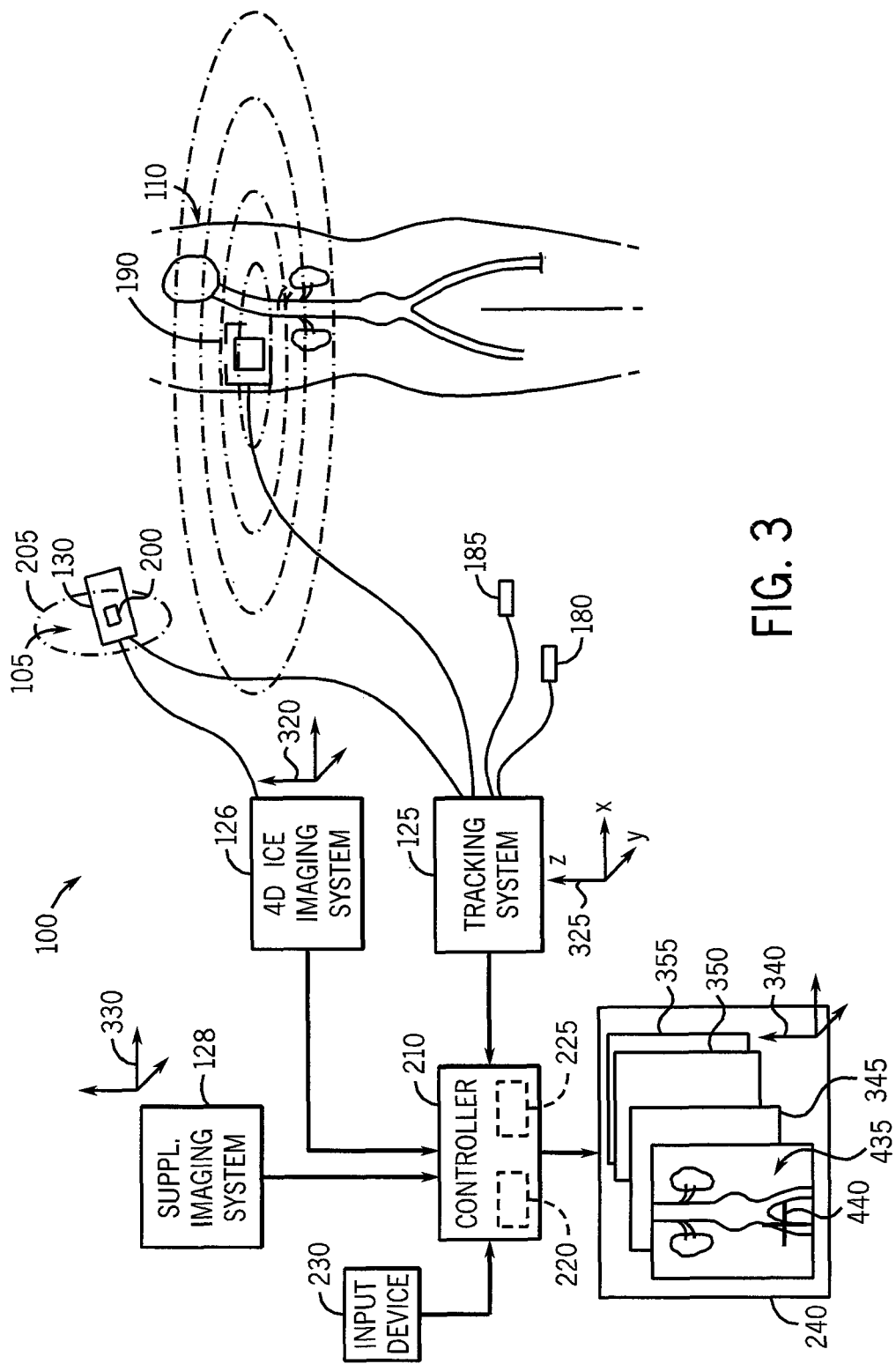
FIG. 3 illustrates a more detailed schematic diagram of the tracking system in combination with the imaging system of the system described in FIG. 1.

Referring now to FIGS. 1 and 3, the tracking system 125 is generally operable to track or detect the position of the tool 105 and the ICE catheter 130 relative to the acquired image generated by the image acquiring system 115. As illustrated in FIG. 3, an embodiment of the tracking system 125 includes an array or series of sensors or tracking elements 180, 185, and 190 connected (e.g., via a hard-wired or wireless connection) to communicate position data to a controller (See FIG. 1). Yet, it should be understood that the number of tracking elements 180, 185, and 190 can vary. For sake of example, assume the tracking elements 180, 185, and 190 include transmitters or dynamic references 180 and 185 in communication or coupled (e.g., RF signal, optically, electromagnetically, etc.) with one or more receivers 190. The number and combination of transmitters and receivers can vary. Either the transmitters 180 and 185 or the receiver 190 can define the reference of the spatial relation. An embodiment of the receiver 190 is detachably connected at and moves with a table in support of the imaged subject 110.

Referring now to FIGS. 1, 2 and 3, an embodiment of the tool 105 and ICE catheter 130 includes a tracking element 200 of the tracking system 125 in communication or coupled with the receiver 190. As shown in FIG. 2, an embodiment of the transmitter 200 generally includes a series of coils that define the orientation or alignment of the ICE catheter 130 about a rotational axis (generally aligned along the longitudinal axis 144) of the ICE catheter 130. Referring to FIG. 3, the transmitter 200 is located integrally with the ICE catheter 130 and is generally operable to generate or transmit a magnetic field 205 to be detected by the receiver 190 of the tracking system 125. In response to passing through the magnetic field 205, the receiver 190 generates a signal representative of a spatial relation and orientation relative to the transmitter 200. Yet, it should be understood that the type or mode of coupling, link or communication (e.g., RF signal, infrared light, magnetic field, etc.) operable to measure the spatial relation varies. The spatial relation and orientation of the transmitter 200 is mechanically defined and known in relation relative to a feature (e.g., a tip) of the ICE catheter 130. Thereby, the tracking system 125 is operable to track the position and orientation of the ICE catheter 130 navigating through the imaged subject 110. Alternatively, the receiver 190 can be attached at the ICE catheter 130 and in communication to measure a spatial relation with transmitters 180 or 185 located remote from the ICE catheter 130.

Alternatively, the transmitters 180, 185 or 200 can include a plurality of coils (e.g., Hemholtz coils) operable to generate a magnetic gradient field to be detected by the receiver 190 of the tracking system 125 and which defines an orientation of the ICE catheter 130. An embodiment of the receiver 190 includes at least one conductive loop operable to generate an electric signal indicative of spatial relation and orientation relative to the magnetic field generated by the transmitters 180, 185 and 200.

Still referring FIGS. 1, 2 and 3, a controller or workstation computer 210 is generally connected in communication with the imaging system 115 (e.g., the ICE imaging system 126 and static imaging system 128) and the tracking system 125. An embodiment of the controller 210 includes a processor 220 in communication with a memory 225. The processor 220 can be arranged independent of or integrated with the memory 225. The processor 220 is generally operable to execute the program instructions representative of acts described herein and stored in the memory 225. The processor 220 can also be capable of receiving input data or information or communicating output data. Examples of the processor 220 can include a central processing unit of a desktop computer, a microprocessor, a microcontroller, or programmable logic controller (PLC), or the like or combination thereof.

An embodiment of the memory 225 generally comprises one or more computer-readable mediums such as a hard disk, a floppy disk, CD, CD-ROM, DVD, compact storage medium, flash memory, random access memory, read-only memory, programmable read-only memory, memory stick, or the like or combination thereof. The memory 225 is operable to store the plurality of program instructions for execution by the processor 220. The memory 225 is also operable to store data generated or received by the controller 210.

The controller 210 further includes or is in communication with an input device 230 and output device 240. The input device 230 is generally operable to receive and communicate information data from user to the controller 210. The input device 230 can include a mouse device, pointer, keyboard, touch screen, microphone, or other like device capable of receiving a user directive. The output device 240 is generally operable to illustrate output data for viewing by the user. An embodiment of the output device 240 is operable to simultaneously illustrate or fuse static or real-time image data generated by the image acquiring system 115 (e.g., the ICE imaging system 126 and static imaging system 128) with tracking data generated by the tracking system 125. The output device 240 is capable of illustrating two-dimensional, three-dimensional image and/or four-dimensional image data through shading, coloring, and/or the like. Examples of the output device 240 include a cathode ray monitor, a liquid crystal display (LCD) monitor, a touch-screen monitor, a plasma monitor, or the like or combination thereof.

Having provided a description of the general construction of the system 100, the following is a description of a method of operating of the system 100 in relation to the imaged subject 110. Although an exemplary embodiment of the method is discussed below, it should be understood that one or more acts or steps constituting the method could be omitted or added. It should also be understood that one or more of the acts can be performed simultaneously or at least substantially simultaneously, and the sequence of the acts can vary. Furthermore, it is embodied that at least several of the following acts can be represented as a series of modules of computer-readable program instructions to be stored in the memory 225 of the controller 210 for execution by the processor 220.

Referring now to FIGS. 2 and 3 and for sake of example, assume that the spatial relation and orientation of the image data acquired by the transducer array 132 of the ICE imaging system 126 is defined by an image coordinate system 320 referenced in predetermined spatial relation and orientation relative to the transducer array 132 (See FIG. 2) at the ICE catheter 130. The image coordinate system 320 generally defines the spatial relation of voxels or pixels of image data relative to one another in the generated image frames or models generated by the ICE imaging system 126 in three dimensions relative to time (i.e., four-dimensional image). Also, for sake of example, assume the tracking system 125 utilizes a tracking coordinate system 325 to define the tracking spatial relation and orientation and movement of the tracking elements 180, 185, 190 and 200 relative to one another and to time. For example, the tracking coordinate system 325 references the orientation and spatial relation of the transmitter 200 at the ICE catheter 130 relative to the receiver or reference 190 of the tracking system 125. Although these coordinate systems 320 and 325 are described as Cartesian x-y-z coordinate systems, the type of coordinate systems 320 and 325 (e.g., polar, etc.) can vary. In addition, the origin and orientation of the coordinate systems 320 and 325 can vary. Also assume that the spatial relation and orientation of the transmitter 200 relative to the ultrasonic transducer array 132 (See FIG. 2) is known or preoperatively measured.

The method includes registering the image coordinate system 320 with the navigation or tracking coordinate system 325. Registering includes measuring (e.g., mechanically or optically) or calculating the spatial relation and orientation of the transmitter 200 relative to the transducer array 132 and in correlation relative to the image coordinate system 320. The method further includes measuring the spatial relation and orientation of the transmitter 200 relative to the reference of the tracking coordinate system 325, which for sake of example assume is the tracking element 190 (e.g., receiver). Although not required, the tracking coordinate system 325 can be defined or can be coincident with a world coordinate system 340 for the system 100. In the foregoing description, assume the world coordinate system 340 of the system 100 and the tracking coordinate system 325 are identical.

As the tracking element 200 and transducer array 132 move with the ICE catheter 130 through the imaged subject 110, the tracking element 200 is linked in electromagnetic communication so as to allow the tracking system to track a location or movement of the tracking element 200 and attached transducer array 132 of the ICE catheter 130 relative to the other tracking elements 180, 185 and 190 and tracking coordinate system 325 for communication via a wireless or wired connection to the controller 210. Based on the signals from all or some of the tracking elements 180, 185, 190, 200, the controller 210 automatically continuously or periodically updates this measured spatial relation to track movement of the transducer array 132 at the ICE catheter 130 relative to the imaged subject 110 and thereby align or display acquired data represented in the four-dimensional model generated by the US imaging system 126 relative to the tracking coordinate system 325, the world coordinate system 340, and/or the imaged subject 110.

The method also includes registering any real-time, acquired image frame 345 with the world coordinate system 340. With the ability to correlate acquired image data or frames with the time, the ICE imaging system 126 is operable to correlate each real-time acquired frame with a tracked cardiac cycle 342 or respiratory cycle 343 (See FIG. 1) of the imaged subject 100 (described in more detail below).

An embodiment of the above-described method can be represented as computer readable program instructions for execution by the processor 220 of the controller 210. Any real-time acquired image data or models generated by the ICE imaging system 126 can be denoted with an absolute time or a relative cardiac phase (ti) and an ICE catheter 130 location (pi) as tracked by the tracking system 125 and is registered to the world coordinate system 340 through the following rigid body transformation:

[T(ice.pi relative to wcs)].ti=[T(ice.pi relative to scs).ti T(scs relative to wcs)], where T(ice.pi relative scs).ti represents registration of the ICE transducer coordinate system 320 at a time or cardiac phase (ti) to the tracking coordinate system 325; T(scs relative to wcs) represents registration of the tracking coordinate system 325 with the world coordinate system 340; [T(ice.pi relative to wcs)].ti represents a registered, real-time three-dimensional ICE image frame 345 acquired at ICE catheter location (pi) and correlated to the time interval or cardiac phase (ti) relative to the world coordinate system 340. After completing the above-described registration, the output device 240 is operable to illustrate the real-time, acquired image frame 345 correlated to the time interval or cardiac phase (ti) superimposed with a full-view, four-dimensional model 350 generated by the ICE imaging system 126 in the world coordinate system 340.

Assume for sake of example that the acquired image data in a two- or three-dimensional model 355 generated from the pre-operative/intra-operative image data acquired by the supplemental imaging system 128 has coordinate system 330. The method further includes registering the world coordinate system 340 that now defines the spatial relation and orientation of the image data of the four-dimensional model 350 (i.e., three-dimensional image model correlated to time) with the second image coordinate system 330 that defines a spatial relation of image data in the model 355 (e.g., two-dimensional, three-dimensional model) correlated to phase of cardiac or respiratory cycle and acquired or generated with the pre-operative or intra-operative imaging system 128 (e.g., MRI, CT, PET, etc.).

Assume for sake of example that the image data of four-dimensional model 350 (i.e., three-dimensional image model correlated to time) generated by the ICE imaging system 126 and the image data of the model 355 acquired or generated with the pre-operative or intra-operative imaging system (e.g., EP, MRI, CT, PET, etc.) 128 are acquired in the same phase (ti) of the cardiac cycle 342 or respiratory cycle 343 tracked by the system 100 (described in more detail below).

According to one embodiment, a graphic user interface (GUI) is configured for illustration to facilitate registration of the four-dimensional model 350 generated by the ICE imaging system 126 with the image data of the model 355 acquired or generated with the pre-operative or intra-operative imaging system (e.g., EP, MRI, CT, PET, etc.) 128. From the GUI, the operator can select from the model(s) 355 generated by one or more supplemental imaging system(s) 128 and that may be stored in a picture archival system (PACS).

The following description of the method can be represented as program instructions for execution by the controller 210. Assume the image data of the model 355 is correlated to a timing sequence, such that the controller 210 can extract a surface view of the imaged anatomy from the pre-operative/intra-operative model 355 created or generated in correlation to or dependent on cardiac or respiratory cycles 342 and 343, herein denoted by [T(pre.3D.surf relative to ics).t1, . . . [T(pre.3D.surf relative to ics)].tn, where "ics" refers to the pre-operative/intra-operative coordinate system 330. The surface view of the pre-operative/intra-operative model 355 may be restricted to a vascular vessel or chamber of interest, or may include nearby anatomical structures, such as the aorta or coronary sinus that are visible in both the pre-operative/intra-operative model 355 and the real-time, acquired ICE image succession of image frames or model 350.

The controller 210 is operable to interpolate image data of the four-dimensional model 350 generated by the ICE imaging system 126 onto a volumetric mesh or grid with the same voxel representation as the model 355 generated by the pre-operative/intra-operative imaging system 128.

From illustration of the GUI at the output device 240 and input device 230, the operator selects a series of points (e.g., pixels, voxels, etc.) on the surface view of the three-dimensional ICE image model 350, denoted as [T(ice.3D.surf relative to wcs)].ti acquired in the selected cardiac phase (ti) (e.g., at the diastole phase) of the cardiac cycle 342. Assume the series of points selected are at anatomical landmarks that can be detected or identified in each of the models 350 and 355.

Also from the GUI, the operator selects a series of points (e.g., pixels, voxels, etc.) from the three-dimensional pre-operative/intra-operative model 355, denoted as [T(pre.3D.surf relative to ics)].ti acquired in the same selected cardiac phase (ti) of the cardiac cycle 342 as that described above. Assume these series of points are selected close to the same anatomical landmarks as those described above.

The controller 210 then aligns the image data of the models 350 and 355 according to the series of points selected relative to the world coordinate system 340, creating a superimposed display for a selected cardiac or respiratory phase (ti) of the respective cardiac or respiratory cycle 342, 343 for visualization or illustration at the output device 240.

A similar method is used to register a remainder of the two models 350 and 355 relative to the world coordinate system 340. The method can further include refinement of the alignment of the models 350 and 355 using mutual information registration (MIR) or automatic image registration (AIR) or other equivalent method.

Alternatively, the method can include display of the four-dimensional ICE model 350 individually and spaced apart from the three-dimensional pre-operative/intra-operative model 355. Once the models 350 and 355 are registered relative to one another, the controller 210 is operable to manipulate (e.g., rotate, zoom, slice, etc.) the models 350 and 355 in synchronization with one another.

The method further includes displaying the tracked location of the tool 105 or ICE catheter 130 in spatial relation and orientation relative to and simultaneously with the four-dimensional model 350 generated by the ICE imaging system 126 and the pre-operative/intra-operative model 355 to create an output display 435 for illustration to and viewing by the physician or clinician performing a medical procedure. It should be understood that the four-dimensional model 350 generated by the ICE imaging system 126 can be combined, (e.g., side-by-side illustration, fused, overlayed or superimposed, etc.) with the various types of diagnostic, interventional, static, or real-time images or models 355 generated by various examples of supplemental imaging technology 128 described above.

Various types of graphics, such as a line, arrow, cursor, triangle, square, cross-hairs, etc. can be used to illustrate a graphic virtual image (illustrated as cross-hairs and by reference 440) of the tool 105 or ICE catheter 130 in simultaneous illustration with the four-dimensional model 350 generated by the ICE imaging system 126. With the ability to track and register movement of the tool 105 or ICE catheter 130 relative to imaging systems, the physician can more safely perform delicate procedures without damaging critical surrounding structures such as arteries and nerves that years ago would have been considered impossible.

An embodiment of the act or step of generating the output display 435 can include illustrating the tracked location of the tool 105 or ICE catheter 130 in spatial relation and orientation relative to and simultaneously with the four-dimensional model 350 generated by the ICE imaging system 126 and the pre-operative/intra-operative model 355, the above synchronized in time with the electrophysiological signals (e.g., cardiac cycle 342, respiratory cycle 343, etc.) for visualization relative to the world coordinate system 340 at the output device 240.

The controller 210 is operable to track movement of the tool 105 or ICE catheter 130 via the tracking system 125 in accordance with known mathematical algorithms programmed as program instructions of a software for execution by the processor 220 of the controller 210. An exemplary navigation software is INSTATRAK® as manufactured by the GENERAL ELECTRIC® Corporation, and NAVIVISION® as manufactured by SIEMENS® and BRAINLAB®. The virtual image 440 of the tool 105 or ICE catheter 130 in spatial relation to the four-dimensional model 350 generated by the ICE imaging system 126 can appear on one or more output devices 240 to guide the physician during delicate procedures.

Referring back to FIG. 1, having described registration of the ICE imaging system 126 with the tracking system 125, the method can be further extended to registering the ICE imaging system 126 and tracking system 125 with other components of the system 100, including an ablation catheter system 450, electrophysiological system(s) (e.g., cardiac monitoring system, respiratory monitoring system, etc.) 460, and a steering system 500 of the tool 105 or ICE catheter 130.

An embodiment of the ablation system 450 has an ablation catheter 452 that is operable to work in combination with the ICE imaging system 126 to ablate or end electrical activity of tissue. An embodiment of the object 105 can include the ablation catheter 452. An embodiment of an electrophysiological system(s) 460 is connected in combination with the ICE imaging system 126 is to track or monitor the cardiac cycle or respiratory cycle of imaged subject 110 correlated to the image data or three-dimensional models acquired or generated by the ICE imaging system 126. An embodiment of a catheter steering system 500 is generally operable to steer or drive movement and changes in direction of the ICE catheter 130 and attached transducer array 132 and transmitter 200 through the imaged subject 110. The steering system 500 can also be operable to drive rotation of the motor 134 in rotating or moving an orientation of the transducer array 132 about the rotational axis 144. This embodiment of extending the method of registering to a steering system 500 is generally similar to the method of registering described above directed to the ICE imaging system 126 with the tracking system 125.

A technical effect of the above-described system 100 and method described above is an ability to register, a four dimensional ICE catheter system 126 with a tracking system 125 and another type of imaging system 128 via execution of computer readable program stored and executable at the controller 210. The controller 210 is operable to perform registration of the coordinate systems 320, 325, 330, 340, 505, relative to one another. Another technical effect of the system 100 and method described above is an ability to combined imaged data and models generated by the ICE imaging system 126 with location of the tool 105 or ICE catheter 130 being tracked by tracking system 125, all in combination with imaged data or models generated by another imaging system 128 operable to compensate for deficiencies in the imaged data acquired with the ICE imaging system 126. Accordingly, the system 100 and method provides for enhanced tracking and guidance of the position and orientation of the tool 105 or the transducer array 132 at the catheter 130 navigating through the imaged subject 110. The system 100 and method also provides for synchronizing the tracking and guidance of movement and orientation of the tool 105 or ICE catheter 130 or ablation catheter 452 associated with the ablation system 450, with each other as well as with electrophysiological signals (e.g., respiratory cycle, cardiac cycle, etc.) as tracked by the electrophysiological system(s) 460.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A system to navigate an image-guided object comprising a tracking element and a transducer array configured to travel in an area of interest of an imaged subject in relation to an acquired image of the imaged subject, comprising:

a four-dimensional (4D) imaging system comprising the image-guided object and configured to acquire first image data, the 4D imaging system further configured to use the first image data to create a 4D model representative of a time-dependent three-dimensional spatial model correlated to a time interval and defined in spatial relation and orientation relative to a first image coordinate system defined by a predetermined spatial relation and orientation of the first image data relative to the transducer array, wherein the time interval is one of a cardiac cycle or a respiratory cycle;

a tracking system comprising sensors, the tracking system configured to track movement and orientation of the image-guided object through the imaged subject relative to a tracking coordinate system defined by the spatial relations and orientations of the sensors to the tracking element and to time; and a second imaging system different than the image-guided object, the second imaging system configured to acquire second image data, the second imaging system configured to use the second image data to create a three-dimensional (3D) model of the imaged subject correlated to a second image coordinate system defined by a spatial relation and orientation of the second image data correlated to a phase of the cardiac cycle or a phase of the respiratory cycle;

a controller electrically connected in communication with the 4D imaging system, the second imaging system, and the tracking system, the controller having a processor configured to:

correlate the 4D model to a world coordinate system, the step of correlating further comprising:
performing a first registration of first image coordinate system with the tracking coordinate system; and
performing a second registration of the tracking coordinate system with a world coordinate system, wherein the world coordinate system defines a spatial orientation of image pixels or voxels within a display;

register the 4D model correlated with the world coordinate system to the 3D model, the step of registering further comprising:
allowing a user to select a series of anatomical landmarks within the 3D model displayed on a graphical user interface (GUI); and
allowing the user to select a series of anatomical landmarks within a portion of the 4D model acquired in the phase of cardiac or respiratory cycle that corresponds to the phase of cardiac or respiratory cycle of the 3D model based on a time reference, the GUI configured to allow the user to select the series of anatomical landmarks within the 4D model; and combine the first image data of the 4D model and the second image data of the 3D model according to the series of anatomical landmarks selected within the 3D and 4D models.

2. The system of claim 1, wherein the image-guided object further comprises a catheter and a motor-driven transducer array operable to acquire the first image data of the imaged subject to create the four-dimensional model by the 4D imaging system.

3. The system of claim 1 wherein the image-guided object further comprises an intracardiac diagnostic or a therapy catheter.

4. The system of claim 1, wherein the four-dimensional model and the three-dimensional model and the tracked location of the image-guided object are all synchronized with respect to the time interval.

5. The system of claim 1, wherein the one of the cardiac cycle and the respiratory cycle are tracked simultaneously with acquiring the first image data by the 4D imaging system.

6. The system of claim 1, wherein the step of combining the first image data of the four-dimensional model and the second image data of the three-dimensional model further comprises one of the group consisting of: synchronizing, aligning, illustrating side-by-side, superimposing, overlaying and fusing the four-dimensional model and the three-dimensional model.

7. The system of claim 1, wherein the four-dimensional model comprises a succession of two-dimensional images each acquired along a plane generally parallel to the longitudinal axis of the image-guided object.

8. The system of claim 1, wherein the processor is further configured to:
track one of a cardiac cycle and a respiratory cycle of the imaged subject, and
acquire the first image data of the four-dimensional model generated by the 4D imaging system and the second image data of the three-dimensional model generated by the second imaging system at a phase that correlates to a phase (ti) of the one of the cardiac cycle and the respiratory cycle.

9. The system of claim 8, further comprising an ablation system having an ablation catheter, wherein the processor is further configured to:
ablate a tissue of the imaged subject in synchronization with acquiring first image data of one of the four-dimensional model and the second image data of the three-dimensional model and in synchronization relative to one of the cardiac cycle and the respiratory cycle.

10. The system of claim 1, wherein the processor is further configured to:
generate the GUI at an input device connected in communication with the controller, detect selection of the series of anatomical landmarks via the input device on a surface view of the 4D image model,
detect selection of the series of anatomical landmarks via the input device on the three-dimensional model, and
display the combined 4D image model and 3D model relative to the world coordinate system on an output device.

11. The system of claim 1, wherein the image-guided object further comprises:
a catheter having a transducer array configured to acquire and communicate the image data to the 4D imaging systems;
a catheter steering system configured to steer changes in a direction of the catheter; and
a motor controller configured to drive rotation of a motor by rotating an orientation of the transducer array about a rotational axis.

12. A method of navigating a tool comprising a tracking element and a transducer array through an area of interest of an imaged subject using a tracking system comprising sensors, the method comprising:
acquiring first image data of a region of interest of an imaged subject with the tool;
generating a four-dimensional (4D) model of the region of interest of the imaged subject based on the first image data acquired with the tool, the 4D model correlated to a time reference and a first image coordinate system defined by a predetermined spatial relation and orientation of the first image data relative to the transducer array;
tracking movement and orientation of the tool traveling through the imaged subject relative to a tracking coordinate system defined by the spatial relations and orientations of the sensors to the tracking element and to time;

acquiring second image data of the region of interest of the imaged subject with a second imaging system different than the tool;

generating a three-dimensional (3D) model of the imaged subject based on the second image data acquired by the second imaging system, the 3D model of the imaged subject correlated to a second image coordinate system defined by a spatial relation and orientation of the second image data correlated to a phase of cardiac or respiratory cycle;

correlating the 4D model to a world coordinate system, the step of correlating further comprising:
performing a first registration of the first image coordinate system with the tracking coordinate system; and
performing a second registration of the tracking coordinate system with a world coordinate system, wherein the world coordinate system defines a spatial orientation of image pixels or voxels within a display;

registering the 4D model correlated with the world coordinate system to the 3D model, the step of registering further comprising:
allowing a user to select a series of anatomical landmarks within the 3D model displayed on a graphical user interface (GUI); and
allowing the user to select a series of anatomical landmarks within a portion of the 4D model acquired in the phase of cardiac or respiratory cycle that corresponds to the phase of cardiac or respiratory cycle of the 3D model based on a time reference, the GUI configured to allow the user to select the series of anatomical landmarks within the 4D model; and
combining the first image data of the 4D model and the second image data of the 3D model according to the series of anatomical landmarks selected within the 3D and 4D models.

13. The method of claim 12, wherein the step of correlating the four-dimensional model and the three-dimensional model relative to the time reference further comprises synchronizing relative to the group consisting of a cardiac cycle and a respiratory cycle tracked simultaneously.

14. The method of claim 12, wherein the one of the cardiac cycle and the respiratory cycle are tracked simultaneously with a of acquiring the first image data by the 4D imaging system to generate the four-dimensional model.

15. The method of claim 12, wherein the step of combining the first image data of the four-dimensional model and the second image data of the three-dimensional model further comprises one of the group consisting of: synchronizing, aligning, illustrating side-by-side, superimposing, overlaying and fusing the four-dimensional model and the three-dimensional model.

16. The method of claim 12, wherein the four-dimensional model comprises a succession of two-dimensional images each acquired along a plane generally parallel to the longitudinal axis of the tool.

17. The method of claim 12, the method further comprising the of:
tracking one of a cardiac cycle and a respiratory cycle of the imaged subject, and
acquiring one of the first image data of the four-dimensional model generated by the 4D imaging system and the second image data of the three-dimensional model generated by the second imaging system at a phase that correlates to a phase (ti) of the one of the cardiac cycle and the respiratory cycle.

18. The method of claim 16, wherein the tool further comprises:
a catheter having a transducer array configured to acquire and communicate the image data to the 4D imaging system;
a catheter steering system configured to steer changes in a direction of the catheter; and
a motor controller configured to drive rotation of a motor by rotating an orientation of the transducer array about a rotational axis of the tool.

19. The method of claim 12, the method further comprising the steps of:
generating the GUI at an input device connected in communication with a controller;
detecting selection of the series of anatomical landmarks via the input device on a surface view of the 4D image model;
detecting selection of the series of anatomical landmarks via the input device on the three-dimensional model; and
displaying the combined 4D image model and 3D model relative to the world coordinate system on an output device.

20. The method of claim 12, the method further comprising the step of:
registering the 4D imaging system and the tracking system relative to a diagnostic or therapy catheter system.

* * * * *